United States Patent
Doukas et al.

(10) Patent No.: US 6,428,532 B1
(45) Date of Patent: Aug. 6, 2002

(54) SELECTIVE TISSUE TARGETING BY DIFFERENCE FREQUENCY OF TWO WAVELENGTHS

(75) Inventors: Apostolos Doukas, Belmont; Shun Lee, Boston, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/460,860

(22) Filed: Dec. 14, 1999

Related U.S. Application Data
(60) Provisional application No. 60/114,271, filed on Dec. 30, 1998.

(51) Int. Cl.[7] ............................................... A61B 18/18
(52) U.S. Cl. ............................... 606/9; 606/10; 606/11; 606/33; 359/245; 359/325; 359/326; 359/349; 372/21
(58) Field of Search ........................... 606/3, 8–10, 13, 606/27, 131, 41, 43, 49; 607/88, 89, 96, 97; 128/898; 359/245–249, 251, 264, 325, 326, 349; 372/21, 22

(56) References Cited

U.S. PATENT DOCUMENTS

| | | | |
|---|---|---|---|
| 3,942,531 A | | 3/1976 | Hoff et al. .................. 128/328 |
| 4,672,969 A | * | 6/1987 | Dew .......................... 128/397 |
| 4,827,911 A | | 5/1989 | Broadwin et al. ......... 128/24 A |
| 4,854,320 A | * | 8/1989 | Dew et al. .................. 128/397 |
| 5,022,757 A | | 6/1991 | Modell ....................... 356/318 |
| 5,209,221 A | | 5/1993 | Riedlinger ............. 128/24 AA |
| 5,500,009 A | * | 3/1996 | Mendes et al. ............... 607/88 |
| 5,553,618 A | | 9/1996 | Suzuki et al. ............ 128/653.1 |
| 5,586,981 A | * | 12/1996 | Hu ................................ 606/9 |
| 5,601,526 A | * | 2/1997 | Chapelon et al. .............. 601/3 |
| 5,725,522 A | * | 3/1998 | Sinofsky ........................ 606/8 |
| 5,882,302 A | | 3/1999 | Driscoll, Jr. et al. ........ 600/371 |
| 5,993,389 A | | 11/1999 | Driscoll, Jr. et al. ........ 600/371 |
| 6,106,514 A | * | 8/2000 | O'Donnell, Jr. ............... 606/9 |

OTHER PUBLICATIONS

"Ultrasound–Mediated Transfection of Mammilian Cells", Hee Joong Kim, et al., Human Gene therapy 7:1339–1346 (Jul. 10, 1996).

"A Review of In Vitro Bioeffects of Inertial Ultrasonic Cavitation from a Mechanistic Perspective", Morton W. Miller, et al., Ultrasound in Med. & Biol., vol. 22, No. 9, pp. 1131–1154, 1996.

"Transient Cavitation in Tissues During Ultrasonically Induced Hyperthermia", F. Graham Sommer, et al., Med. Phys. vol. 9, No. 1, Jan./Feb. 1982, pp. 1–3.

(List continued on next page.)

*Primary Examiner*—Linda C. M. Dvorak
*Assistant Examiner*—A. Farah
(74) *Attorney, Agent, or Firm*—Nutter McClennen & Fish LLP (57) ABSTRACT

A method and apparatus for treating tissue directs first and second wavelengths of energy, e.g., laser or ultrasonic signal energy, into an overlap region of tissue such that the first and second wavelengths mix in situ to form a third wavelength. The third wavelength effectively couples energy into the tissue to treat tissue in said overlap region, producing local heating or cavitation. Wavelengths may be selected such that overlying tissue is unharmed, and the two wavelengths may be applied along different paths and cross in the overlap region. Absorbers or dyes may be used to tailor absorbance of the third wavelength. When using ultrasonic energy, signals of several megahertz may be so mixed to provide a lower frequency treatment signal such as a 200 kHz treatment signal or a subharmonic. Laser signals may be mixed to form a treatment signal in the infrared.

25 Claims, 1 Drawing Sheet

OTHER PUBLICATIONS

"Cavitation–Generated Free Radicals During Shock Wave Exposure: Investigations with Cell–Free Solutions and Suspended Cells", Dierk Suhr, et al., Ultrasound in Med. & Biol. vol. 17, No. 8, pp. 761–768, 1991.

"Ultrasound Contrast Agents Nucleate Inertial Cavitation In Vitro", Douglas L. Miller, et al., Ultrasound in Med. & Biol., vol. 21, No. 8, pp. 1059–1065, 1995.

"Free Radical Production by High Energy Shock Waves–Comparison with Ionizing Irradiation", Thomas R. Morgan, et al., The Journal of Urology, vol. 139, 1988.

"Stable Cavitation at Low Ultrasonic Intensities Induces Cell Death and Inhibits $^3$H–TdR Incorporation by Con–aStimulated Murine Lymphocytes In Vitro", Alfred A. Vivino et al., Ultrasound in Med. & Biol., vol. 11, No. 5, pp. 751–759, 1985.

"A Piezocomposite Shock Wave Generator with Electronic Focusing Capability: Application for Producing Cavitation-Induced Lesions in Rabbit Liver", Jahangir Tavakkoli, et al., Ultrasound in Med. & Biol., vol. 23, No. 1, pp. 107–115, 1997.

"The Sensitivity of Biological Tissue to Ultrasound", Stanley B. Barnett, et al., Ultrasound in Med. & Biol., vol. 23, No. 6, pp. 805–812, 1997.

"Optics of the Skin", R. Rox Anderson, Harvard Medical School, Boston, Massachusetts, pp. 19–35.

"Ultrasound–Stimulated Vibro–Acoustic Spectrography", Mostafa Fatemi et al., Science, vol. 280, pp. 82–84, 1998.

* cited by examiner

FIG. 1

SELECTIVE TISSUE TARGETING BY DIFFERENCE FREQUENCY OF TWO WAVELENGTHS

CROSS-REFERENCE TO RELATED APPLICATIONS

This application claims priority to U.S. Provisional Patent Application No. 60/114,271 filed Dec. 30, 1998, the contents of which are incorporated herein by reference.

BACKGROUND OF THE INVENTION

Surgical instruments and surgical methods, methods of chemotherapy, radiation therapy and hyperthermic treatment can be utilized for the medical treatment of various proliferating diseases, e.g., tumors and cancer. Methods of acoustic surgery for similar applications have not presently been widely accepted in these areas of clinical practice.

Laser and improved acoustic techniques are under development for surgical techniques. Lasers are currently used for targeted energy delivery in a variety of medical procedures. The absorption of light is function of wavelength. The 600 nm to about the 1200 nm spectral band has been called a "window" region because there is deep penetration of photons into tissue due to low absorption (1). Measurement of the transmission of coherent photons using optical heterodyne detection has been performed for 2–7 mm thick tissue sections (2). The total extinction coefficient $\mu$, (790 nm) of skin, liver, and muscle is 0.96–1.75 $mm^{-1}$. For targeted delivery the laser energy should be preferentially absorbed in the treatment site. One of the most successful medical uses of lasers occurs when endogenous chromophores are located in the treatment region. Unfortunately selective concentration of endogenous chromophores in the treatment location occurs rarely. Therefore exogenous chromophores that are preferentially delivered into the treatment site are currently under investigation (3).

For acoustic surgery, a mechanically oscillated hollow metal pin, for example, can be used as a therapeutic tool. High-power focused ultrasound acoustic fields are able to destroy human body tissue (see PCT published applications in the name of Fry WO 89/07907 and WO98/07909). Dunn and Fry have also described in "Ultrasonic threshold dosage for the mammalian central nervous system" IEEE transactions, volume BME 18, pages 253–256 how this destruction process involves two effects, more a specifically a thermal effect and a cavitation effect.

In general, the thermal effect predominates when the acoustic power at the point of focus is below the threshold of about 150 $W/cm^2$ at MHZ. Therefore, thermal effects are due to the acoustic absorption of the tissue which converts the mechanical energy of the acoustic wave into thermal energy.

More specifically, the cavitation effect becomes predominant when the acoustic power at the point of focus exceeds a threshold of 150 $W/cm^2$. Cavitation is linked to the formation of microscopic bubbles of gas which implode when they reach a critical diameter with a local release of appreciable amounts of energy leading to destruction of neighboring tissue.

In order to obtain destruction of tissue exclusively by thermal effects, it has been necessary for the acoustic field to be able to reach a threshold of destruction referred to as the "thermal dose." This threshold is a function of temperature reached and of the duration of application. Thus the presently known approaches have been to destroy tissue by application of a moderate temperature increase over a long duration of application or, through application of a significant temperature increase over a short period of application.

SUMMARY OF THE INVENTION

The present invention is based, at least in part, on the discovery that by directing two different wavelengths of energy (beams), simultaneously, at a focal point or region within tissue, an overlap region forms having an energy difference which causes selective cavitation and/or hyperthermia in tissue at the site of intersection of the two beams. This localized treatment does not effect tissue surrounding the area where the two beams do not overlap and is, therefore, an effective means to treat tissue, e.g., diseased tissue, without harming the surrounding tissue area about the site of selective cavitation.

The present invention pertains to apparati for treating tissue using two different wavelengths, e.g., energy beams. The apparati include a first energy emitter which produces a first wavelength of energy and a second energy emitter which produces a second wavelength of a second energy. The first and second wavelengths are focused onto a focal point or region of the tissue, so that the first and second wavelengths intersect and produce an overlap region having an energy difference. The energy difference causes cavitation and/or hyperthermia at the focal point or region within the tissue. The two different wavelengths are generated by energy emitters. Suitable energy emitters are lasers, e.g., ND:YAG lasers, or piezoelectric transducers. In a preferred embodiment, the acoustic energy difference between the two energy beams is about 200 kHz with a subharmonic frequency of about 100 kHz.

The present invention also pertains to apparati for treating tissue using two different wavelengths, energy beams, which include a first energy emitter, a second energy emitter and a control means. The first and second energy emitters produce two differing wavelengths. The control means facilitates transmission and focusing of the energy beams onto a focal point or region of the tissue. The energy beams intersect and produce an overlap region which has an energy difference which produces cavitation and/or hyperthermia at the focal point or region within the tissue. The control means causes transmission of cavitation waves, e.g., ultrasound, for a duration of between about 1 milliseconds and continuous. Alternatively, the control means causes hyperthermia when an energy pulse of between about 20 nanoseconds ($10^{-8}$ seconds) and 5 femtoseconds ($10^{-15}$ seconds). The controls means can also provide transmission of ultrasonic waves, light, coherent light, or energy waves which result in hyperthermia by successive pulses.

The present invention further pertains to methods for treating tissue using two different wavelengths simultaneously. The methods include directing a first wavelength of energy into a tissue and directing a second wavelength of a second energy into the tissue, such that the first and second wavelengths are focused onto a focal point or region of the tissue. The first and second wavelengths intersect to produce an overlap region which has an energy difference causing cavitation to occur at the focal point or region within the tissue, thereby treating the tissue. This localized treatment does not effect tissue surrounding the area where the two beams do not overlap and is, therefore, an effective means to treat tissue, e.g., diseased tissue, without harming the surrounding tissue area about the site of selective cavitation.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on the discovery that by directing two different wavelengths of energy (beams), simultaneously, at a focal point or region within tissue, an overlap region forms having an energy difference which causes selective cavitation in tissue at the site of intersection of the two beams. This localized treatment does not effect tissue surrounding the area where the two beams do not overlap and is, therefore, an effective means to treat tissue, e.g., diseased tissue, without harming the surrounding tissue area about the site of selective cavitation.

Two energy waves of frequencies w1 and w2 propagating through a medium will generate at the overlap region (a region where the two waves are present at the same time) a wave of frequency (Dw=w1−w2). This is true for any type of wave (e.g., light or sound). The difference frequency is also known as beat frequency. Many of the interactions of the waves depend on the frequency of the wave. Therefore, the overlap region where the beat frequency is generated, can produce interactions that are unique. This is the basis of selectivity and targeting of tissue of the present invention. The two types of waves that are of interest are laser radiation and ultrasound. Because the way that light and sound affect tissue are fundamentally different, the two methods are presented separately where appropriate. In this invention the beat frequency produced by laser radiation causes elevation of temperature at the overlap region because of increased absorption of the beat frequency by the tissue (hyperthermia). On the other hand, the beat frequency ultrasound causes cavitation which destroy tissue by mechanical lysis and/or the generation of free radicals and/or hyperthermia.

For example, the conversion of light in situ at the treatment site to another wavelength that is strongly absorbed should be considered. The increase in absorption can be dramatic. Water has an absorption that varies from ~$10^{-4}$ (visible light) to ~$10^{-4}$ cm-1 (~3 mm), eight orders of magnitude increase in absorbance (4). One advantage of in situ generation is the ability to target specific chromophores (5). There is another advantage to using two or more beams of photons for treatment. By separation of the energy into two different delivery paths, the treatment site (where the beams intersect) will receive the necessary dose while sparing adjacent tissue.

The conversion of light from one wavelength to another is a phenomenon that is familiar to users of commercially available lasers (e.g., output of 532 nm by second harmonic generation with the 1064 nm from a ND:YAG laser). Another example is the generation of intense and tunable coherent vacuum ultraviolet light (70 run to 200 nm) for molecular spectroscopy (6). The number of photons per pulse exceeds $10^{-10}$–$10^{-11}$ when pulsed dye lasers are used to generate the vacuum ultraviolet light. Light with a different wavelength can be produced by sum and/or difference mixing between as many as three different fundamental frequencies via a third-order nonlinear process (7):
Process $j=1: {}^\omega 1 + {}^\omega 2 + {}^\omega 3 \to {}^\omega 4 \; k_1^- k_2^+ k_3$ $j=2: {}^\omega 1 + {}^\omega 2 + {}^\omega 3 \to {}^\omega 4 \; k_1^- k_2^+ k_3$ $j=3: {}^\omega 1 + {}^\omega 2 + {}^\omega 3 \to {}^\omega 4 \; k_1^- k_2^+ k_3$ $k'' = k_1^+ k_2^+ k_3$ where $\omega_i$ and $k_i$ (for i=1, 2, and 3) are the frequencies and wavevectors of the input; $\omega 4$ and $k_4$ is the frequency and wavevector of the output; and the wave-vector mismatch is $\Delta k \equiv k_4 - k'$. As an example, 3000 nm light can be generated by mixing 1200 nm and 750 nm (via the j=2 process).

The total power generated when two of the input frequencies are degenerate is given by (7)

$$P_4 = (1.580 \times 10^{-4}) \frac{k_4^3 k_1 k_2 k_3}{k_3^2 k} N^2 \chi^2 P_1 P_2 P_3 F_j \left( b\Delta k, \frac{b}{L}, \frac{f}{L}, \frac{k''}{k'} \right), \quad (1)$$

{with P's in W, k's in cm$^{-1}$, b in cm, N in atoms/cm$^3$, $\kappa$ in esu/atom} where $P_i$ (for i=1, 2, and 3) are the power of the input beams, $P_4$ is the power of the output beam; $k_0 = nk_4$ is the wave vector of the generated radiation in vacuum, $$b \equiv \frac{2\pi \omega_0^2}{\lambda} = \frac{2\pi \omega_0^2 n}{\lambda_0} = \frac{2\lambda_0}{n\theta^2} = k\omega_0^2$$

is the confocal parameter, $\omega 0$ is beam-waist radius, f is the focus, L is the length of the nonlinear medium, and the dimensionless function is $$F_j \left( b\Delta k, \frac{b}{L}, \frac{f}{L}, \frac{k''}{k'} \right) \equiv \frac{8}{9} \frac{k_4^2 k}{\pi^3 k_2^4} \frac{1}{b^3 \chi^2 |E_{10} E_{20} E_{30}|^2} \int dR 2\pi R |E_4(R)|^2. \quad (2)$$

Consider the generation of 3000 nm light with a single pulse of 20 mJ (25 ns) 1200 nm and a single pulse 10 mJ (25 ns) 750 run in water. Using the following constants: third-order nonlinear susceptibility for water is $1.44 \times 10^{-36}$ esu (8) $\Delta k=0$; b/L=0.1; f/L=0.5; the dimensionless function $F_2$ is estimated to be 0.01 (7); density of water at 20° C. is 0.99821 g/cm$^3$ (9); molar mass of water at 20° C. is 18.01528 g/mol (9); and $N_A = 6.0221367(37) \times 10^{23}$/mol (9), the total power generated is calculated from Eq. 1 to be $6 \times 10^3$ W or ~162 $\mu$J for 25 ns (~0.5 % conversion). This calculation is for the case of exact phase matching (i.e., $\Delta k=0$). A more detailed calculation would involve positive contributions to $P_4$ from generation of photons with $\Delta k \ne 0$. The increase in tissue temperature can be estimated to be 71° C. from (10) $\Delta T = Q\Delta t / VpC$ where $\alpha=0$, V=628 $\mu$m$^3$, p=1.09 g/cm$^3$, C=0.8 cal/g° C., and Q$\Delta t$=162 $\mu$J.

To determine cell viability as a function of laser parameters, a beam of 1200 nm and a beam of 750 nm light will be focused onto a monolayer of cells. Cell viability will be quantified by the Fluorescein Diacetate/Ethidium Bromide assay. The energy of the two beams will be varied independently. Two other parameters that will be examined is the angle between the beams and focal length.

To determine minimum laser energy needed for photocoagulation, a beam of 1200 nm and a beam of 750 nm light will be focused into skin ex vivo. The energy of the two beams will be varied independently. Biopsies will be obtained for histology. The extend of thermal damage in the tissue will be investigated. This will be repeated for increasing depth of penetration into tissue.

The present invention describes a novel approach to target energy delivery. Light which is delivered via fiber optics can be converted in situ into another wavelength. The ability to generate light with a specific wavelength that is both spatially and temporally localized allows selective targeting of endogenous or exogenous chromophores. Medical instruments that currently incorporate fibers for light delivery may find new uses. The concept of generating light with a different wavelength in situ in a localized region has important implications not only for treatment but also for diagnostic applications.

The two modalities of therapeutic ultrasound or laser treatment are based on hyperthermia, the rise of the local temperature of tissue, and/or cavitation, the formation and collapse of bubbles (11). Bubbles are initiated during the tensile (negative pressure) cycle of energetic waves, such as ultrasound. Once they are formed, they are forced to oscillate in phase with the applied energetic, e.g., ultrasound, pressure, rapidly increasing in size. As the bubble size increases the bubble becomes unstable and implodes. Cavitation is art recognized and is a violent and destructive phenomenon. During the collapse of the bubble, temperatures as high as 5000° C. and pressures of hundreds of atmospheres can be generated. The energy released during cavitation is sufficient to produce light (sonoluminescence), hydrolysis, free radicals, and chemical reactions (12). Cavitation has been shown to cause injury to cells and tissue either by mechanical lysis or by the generation of free radicals, such as $HO_2.$, OH—, HO., and $H_2O.$, which damage the cell membrane (13). These radical species are identical to those produced in water by ionizing radiation, e.g., Cobalt-60, and are strong oxidizing agents (14).

Cavitation, among the non-thermal effects of energetic beams, e.g., ultrasound, has the greatest potential for therapeutic applications, when controlled. The present invention exploits selective targeting of tissue based on cavitation. Two different energy frequencies are crossed within tissue with the overlap region generating a difference frequency (beat frequency) where the two beams cross. Cavitation, e.g., ultrasonic waves or hyperthermia, e.g., ultrasonic waves and light waves, e.g., laser, occur at the point of intersection of the two beams. The method takes advantage of the fact that the cavitation threshold and/or hyperthermia depends on the frequency of the energetic beam, e.g., laser or ultrasound.

For example, low frequency ultrasound is more effective in producing cavitation than high frequency ultrasound (15). In the present invention, the frequencies of the two ultrasound beams are set above the cavitation threshold. The two beams are made to overlap spatially and temporally inside the target to produce cavitation. For example, if the frequency of two ultrasound beams are 4.0 and 3.8 MHZ, respectively, 200-kHz ultrasound is generated at the overlap region which is more effective in producing cavitation than either the 4.0-MHZ or the 3.8-MHZ ultrasound. Thus, only at the overlap region of the two ultrasound beams and nowhere else in the tissue, will cavitation be produced. The cavitation will cause destruction of tissue either by mechanical lysis or generation of free radicals. The radical species that are generated have short lifetimes and they remain localized in the target area. Therefore, surrounding areas of the tissue will not be affected. Typical pulse durations are between about 1 millisecond and continuous for ultrasonic treatment and between about 2 nanoseconds and 5 femtoseconds for laser treatment.

Acoustic contrast agents essentially contain stable air bubbles. They enhance the echo in diagnostic applications of ultrasound (16). Bubble-based contrast agents have been shown to enhance cavitation during ultrasound exposure (17). In addition, these contrast agents enhance the production of hydrogen peroxide. Therefore, acoustic contrast agents can be used to increase the efficiency of cavitation and provide an additional degree of selectivity. It is of interest to note that high frequency ultrasound (3.8 MHZ) did not produce any cavitation even in the presence of contrast agents (17). Suitable contrast agent include, for example, Albunex® (Molecular Biosystems, San Diego and Levovist®) (Schering AG, Berlin, Germany). Albunex® is a coated microbubble produced by sonication of an albumin solution. Levovist® is made of dry particles of galactose which form a microbubble suspension when water is added.

Ultrasound-induced cavitation is responsible for the permeabilization of the cell plasma membrane (18). The membrane permeabilization is transient and the plasma membrane recovers. The permeabilization of the plasma membrane allows large molecules to diffuse into the cytoplasm. Mammalian cells have been successfully transfected with b-galactosidase in vitro ( 19). In addition, there is evidence that the combination of acoustic contrast agents and ultrasound facilitated transfection in an animal model in vivo (19). Therefore, localized generation of low frequency ultrasound could also be applied to selective sites of an organ or tissue for drug delivery or as a vector for gene therapy.

Although the variety of the tissues to be treated necessitates adaptation of the energy beam parameters, they can be defined quantitatively as follows:

Carrier frequency f of the energy (sonic) pulse signal:
3 MHz<f<5 MHZ

Duration T of the sonic pulse signal:
1 ms<T<continuous

Intensity of sound
20 W/cm² to 200 W/cm²

Recurrence rate r (pulse succession frequency):
100 Hz to continuous

For treating a particular type of tissue, in a predetermined part of the body, the selection of the parameters should be made in the view of clinical experience. For example, the object is to acoustically generate cavitation bubbles in the proliferating cell area to cause mechanically induced significant alterations in the tissue environs and/or alterations in the tissue cells themselves. Such alterations are indicated by a fall in, an obstruction of, or even an interruption of, the blood supply to a cell, as well as by acoustically induced interference with the existing mode of nutrition of the cell, and/or by destruction of the cell elements (rips in the cell membranes, destruction of elements of the cell contents), but not necessarily by destruction of the structural cohesion of the cell aggregate.

In principle, the carrier frequency, the duration of the energy pulse signal and the amplitude and duration of the negative pressure phase, are the essential quantities which determine the cavitation threshold in a preselected tissue. The higher the carrier frequency, the shorter are the sonic pulse and negative pressure phase durations and the lower is the amplitude of the negative pressure phase, the more unlikely will be the onset of cavitation.

In one aspect the present invention pertains to methods for treating tissue using two different wavelengths simultaneously. The methods include directing a first wavelength of energy into a tissue and directing a second wavelength of a second energy into the tissue, such that the first and second wavelengths are focused onto a focal point or region of the tissue. The first and second wavelengths intersect to produce an overlap region which has an energy difference causing cavitation and/or hyperthermia to occur at the focal point or region within the tissue, thereby treating the tissue. This localized treatment does not effect tissue surrounding the area where the two beams do not overlap and is, therefore, an effective means to treat tissue, e.g., diseased tissue, without harming the surrounding tissue area about the site of selective cavitation.

The terms "treat", "treatment" or "treating" is intended to cover both prophylactic and/or therapeutic applications. The methods of the invention can be used to protect a subject from damage or injury caused by disease, or can therapeutically treat the subject after to the onset of a disease.

The term "subject" is intended to include mammals susceptible to diseases, including one or more disease related symptoms. Examples of such subjects include humans, dogs, cats, pigs, cows, horses, rats, and mice.

The term "disease" is associated with an increase of a pathogen within a subject such that the subject often experiences physiological symptoms which include, but are not limited to, release of toxins, gastritis, inflammation, coma, water retention, weight gain or weight loss and immunodeficiency. The effects often associated with such symptoms include, but are not limited to, fever, nausea, diarrhea, weakness, headache, and even death. Examples of diseases which can be treated by the present invention include undesirable cell proliferation, bacterial infection and cancer.

The language "undesirable cell proliferation" is intended to include abnormal growth of cells which can be detrimental to a mammal's physiological well being. Effects of undesirable cell proliferation can include the release of toxins into the mamnmal, fever, gastritis, inflammation, nausea, weakness, coma, headache, water retention, weight gain or weight loss, immunodeficiency, death, etc. The undesired cells which proliferate can include cells which are either benign or malignant. Examples of undesirable cell proliferation include bacterial cell proliferation and aberrant cell division and/or proliferation of foreign cells, such as in cancer cells.

The language "aberrant cell division and/or proliferation" is art recognized and is intended to cover those instances where cells are generated in excess of what is considered typical in physiologically similar environment, such as in cancers.

The term "cancer" is art recognized and is intended to include undesirable cell proliferation and/or aberrant cell growth, e.g., proliferation.

The term "tissue" is art recognized and is intended to include extracorporeal materials, such as organs, e.g., mesentery, liver, kidney, heart, lung, brain, tendon, muscle, etc. and corporeal materials, such as blood cells, e.g., red and white blood cells, and extracellular matrix components.

The term "emitter" is intended to include those devices which produce and transmit an energy beam, e.g., one or more wavelengths, in the form of sound waves, e.g., ultrasonic (ultrasound), or light waves, e.g., coherent light (laser). Suitable means to produce ultrasonic waves include piezoelectric transducers driven by an independent frequency generator, such as quartz or ceramic types. Suitable means for producing coherent light is a laser. Examples of suitable lasers include ND:YAG, optical parameter oscillator, continuously tunable oscillator, mode-locked or titanium sapphire.

The phrase "onto a focal point or region" is intended to mean that the focused wavelengths, e.g., energy beams, are concentrated at a position within the tissue where the two beams intersect. This point of intersection can be controlled such that an area from between about 500 microns to about 10 mm (ultrasonic) or 100 microns to 2 mm (light, e.g., laser) can be treated at the point of intersection. To accomplish this, multiple pairs of energy beams which produce overlap regions can be focused at the locus or, one set of mismatched energy beams can be positioned about the tissue to be treated or, alternatively, one or more pairs of emitters can be moved translationally or rotationally in the X, Y, Z planes. It is to be understood that the energy beams can be attenuated such that the depth of penetration into the tissue can be controlled such that such penetration is superficial or penetrates into the tissue to a predetermined depth.

The phrase "overlap region" refers to the area represented by the intersection of two energy beams.

The phrase "energy difference" is intended to mean the difference in energy between two wavelengths. In one embodiment, two ultrasonic beams can be made to overlap where a first beam is between about 2 MHZ and about 5 MHZ, preferably about 4.0 MHZ and a second beam is between about 2 MHZ and about 5 MHZ, preferably about 3.8 MHZ. In a preferred embodiment, the range for the two beams is between about 2 MHZ and about 3 MHZ. The difference in energy is between about 50 kHz and about 300 kHz, preferably about 200 kHz with a subharmonic frequency of between about one half of the beat frequency, preferably 100 kHz and is generated at the overlap region of the two beams. Alternatively, two laser beams can be made to overlap where a first beam is between about 300 nm and about 2100 nm, preferably 1200 nm and the second beam is between about 300 nm and about 2100 nm, preferably 750 nm. The difference is between about 70 nm and about 8000 nm.

The present invention also pertains to apparati for treating tissue using two different wavelengths, e.g., energy beams, e.g., acoustic waves or coherent light (laser) waves. The apparati include a first energy emitter which produces a first wavelength of energy and a second energy emitter which produces a second wavelength of a second energy. The first and second wavelengths are focused onto a focal point or region of the tissue, so that the first and second wavelengths intersect and produce an overlap region having an energy difference. The energy difference causes cavitation and/or hyperthermia at the focal point or region within the tissue. The two different wavelengths are generated by energy emitters. Suitable energy emitters are lasers, e.g., ND:YAG lasers, or piezoelectric transducers.

The present invention further pertains to apparati for treating tissue using two different wavelengths, energy beams, which include a first energy emitter, a second energy emitter and a control means. The first and second energy emitters produce a two wavelengths of different energies. The control means facilitates transmission and focusing of the energy beams onto a focal point or region of the tissue. The energy beams intersect and produce an overlap region which has an energy difference which produces cavitation and/or hyperthermia at the focal point or region within the tissue. The control means causes transmission of ultrasonic waves for a duration of between about 1 microseconds and continuous. The controls means can also provide transmission of ultrasonic waves by successive pulses.

Figure 1:
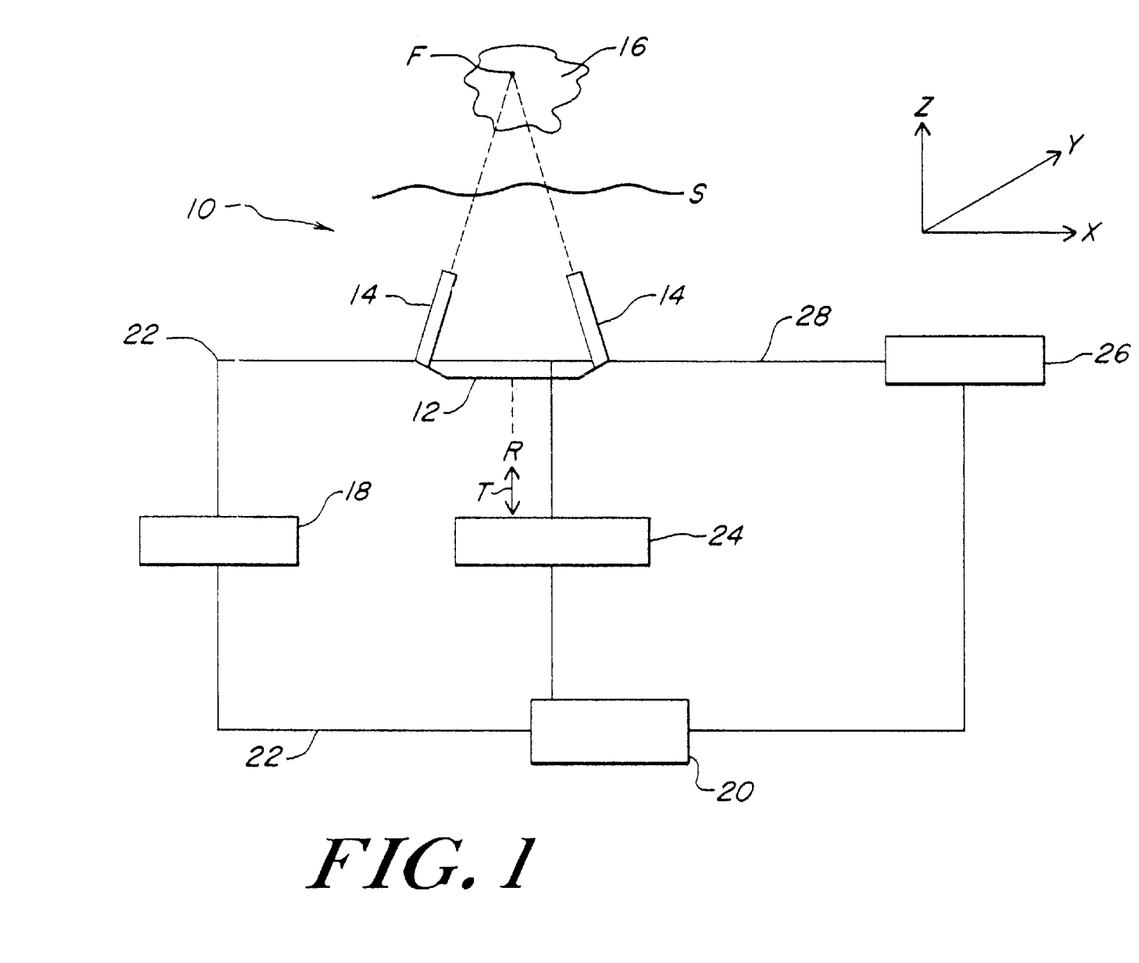
FIG. 1 diagrammatically depicts one embodiment of the present invention.

FIG. 1 depicts an apparatus useful for treating tissue by the methods outlined above. The apparatus is identified by reference number 10. The treatment apparatus includes treatment device number 12. Treatment device 12 includes at least two energy emitters 14, e.g. lasers or piezoelectric transducer elements. Treatment device 12 is designed to treat tissue, shown diagrammatically by general reference number 16. Tissue 16 can be situated inside the body of a mammal, in particular a human being. The skin surface of this mammal is identified by the letter S. Apparatus 10 further includes control means such as 18 and 20 controlling the device 12, as is shown symbolically by the link 22. Energy emitters 14 are preferably designed to deliver ultrasonic waves focused onto a focal point or region F. The point of focus F determines the tissue region which is to be subjected to therapy.

The apparatus is characterized in that it comprises control means 18 and 20 for treatment device 12 designed to cause treatment device 12 to supply energy frequencies of two different energies, having a net difference in energy, thereby producing cavitation selectively in the tissue 16 to be treated. The control means advantageously enable the transmission of ultrasonic waves to be controlled.

In a preferred embodiment, the frequency of cavitation ultrasonic waves is lower than the frequency of thermal ultrasonic waves.

In another embodiment, the control means 18 and 20 provide the transmission of cavitation ultrasound waves for a duration comprised between about 1 millisecond and continuous, preferably between about 100 milliseconds and about 2 minutes.

In one embodiment, control means 18, 20 provide transmission of cavitation ultrasound waves by successive pulses, the repetition frequency of which varies from about 100 Hz to continuous, preferably between about 100 Hz to about 1 kHz.

In another embodiment, the duration of the adjustable predetermined time interval is comprised between about 10 Hz to about 0.01 Hz.

Apparatus 10 can further include means 24 for displacing treatment device 12 in order to perform point-by-point treatment, by the focal point or region F, in order to cover the whole volume of the target 16 to be treated.

Preferably, displacement means 24 of the treatment device 12 are controlled by a control means 18, including, for example, calculating means such a computer or a microcomputer, the latter being preferably provided with software for managing the displacement of treatment device 12 by suitable control of the displacement means 24 along the three coordinates X, Y and Z as a function of the volume of the target to be treated.

Treatment device 12, can be mounted so as to be rotatable about its common axis identified by arrow R and/or in translation along a common axis identified by arrow T, through imaging probe displacement 26 with a link 28. Control means 18 controls, by unit 24, the displacements of treatment device 12 as well as the means 28 for displacing the apparatus, in rotation and/or in translation.

It can thus be seen that the therapy apparatus can be used with, or applied to, all types of therapy using lasers or ultrasound, of all benign of malignant tumors, whether such tumors be internal or external. Applications include the treatment of benign or malignant tumors of the liver, of the prostate, of the kidney, of the breast, of the skin, of the brain and for the treatment of varicose states and of the esophagus.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

Methodology

1. The experimental arrangement consists of two piezoelectric transducers which are driven by two independent frequency generators. The frequencies of the two transducers are set to differ by 50–300 kHz. For example, one transducer will operate at 3.8 MHZ, while the second transducer will be set at 4.0 MHZ. Both ultrasound frequencies are too high to produce cavitation even in the presence of contrast agents (17). The transducers will be inserted into a container filled with water. The two ultrasound beams will be made to overlap at their focal points. The presence of cavitation will be detected by measuring the subharmonic frequency, one half of the ultrasound frequency inducing cavitation. The driving ultrasound frequency in the proposed experimental arrangement is 200 kHz and the subharmonic frequency will be 100 kHz. A hydrophone will be used to measure the subharmonic signal. The signal will be passed through a narrow band filter to remove all other frequencies present. A spectrum analyzer will be used to measure and analyze the signal. The strength of the subharmonic is related to the level of cavitation generated by the ultrasound. In fact, a strong correlation has been found between cell damage and the emitted subharmonic energy in vitro (20). The strength of the subharmonic signal will be measured as a function of the intensity of the two ultrasound beams, the difference frequency, and the concentration of acoustic contrast agents.

The formation of free radicals will be measured indirectly using the Fricke ferrous sulfate dosimeter (14). This assay has been the standard for chemically measuring ionizing radiation and has also been previously used to measure the free radicals generated by extracorporeal shock wave lithotripters (14). The two beams will be made to cross inside an aqueous solution of ferrous sulfate. The ferrous sulfate will be oxidized to ferric ion by the free radicals. The amount of ferric ion produced will be determined by its absorbance at 224 nm in a spectrophotometer. The Fricke dosimeter will be calibrated against an ionizing radiation source (14). The amount of ferric ion will be determined as a function of the intensity of the two ultrasound beams, the difference frequency, and the concentration of acoustic contrast agents. The amount of ferric ion will also be compared to the strength of the subharmonic frequency.

2. The damage threshold will be determined in an organ (liver) ex vivo. The two transducers will be acoustically coupled to the organ with acoustical gel. The two ultrasound beams will be made to overlap inside the organ. The hydrophone will be inserted into the organ to measure the intensity of the subharmonic frequency. The intensity of the subharmonic measures the generation of cavitation. The threshold intensity will also be measured by acoustic contrast agents that will be injected into the organ prior to the experiments. In addition, biopsies from the overlap regions as well as regions exposed to one beam only will be taken for histological examination. These experiments will determine the cavitation threshold in an organ and the nature and the degree of damage.

3. The two ultrasound beams will be made to overlap inside a tube through which cells can be flown. In this arrangement, the time of cell exposure can be controlled by adjusting the flow rate. Red blood cells (RBC) will be used in these experiments. RBC have been extensively used in studies of molecular loading with ultrasound (8), extracorporeal lithotripters (21), and laser-generated stress waves (22). Cavitation will permeabilize the plasma membrane of RBC and allow hemoglobin to diffuse out of the cell. The amount of hemoglobin released will be measured by measuring the absorbance of the collected medium at 420 nm (absorption band of hemoglobin). In addition, the number of cells will be measured before and after the experiment to determine the degree of cell lysis. The hemoglobin efflux will be determined as a function of the ultrasound intensity, time of exposure, and concentration of contrast agents. Control experiments will also be performed in which RBC will be exposed only to one ultrasound beam under otherwise identical conditions.

The two ultrasound beams will be made to overlap in a tube through which cells are flown. The flow rate will determine how long the cells are exposed to the difference frequency. RBC and lymphocytes will be used in these experiments. These cells have been selected because we have experience with preparation and handling. In addition, we have a good understanding of how they respond to mechanical forces. RBC exposed to ultrasound will permeabilize and allow hemoglobin to diffuse out of the cell. The amount of hemoglobin released will be measured by measuring the absorbance of the medium. The hemoglobin efflux will be determined as a function of the ultrasound intensity and flow rate. In addition to the efflux the influx of molecules present in the extracellular medium can be determined. Both RBC and lymphocytes will be used in the experiments. The cells will be flown in the tube and exposed to the difference frequency. Probe molecules (labeled dextran of 4, 12 and 70 kDa) will be added to the extracellular medium. The uptake of the molecular probes will be determined by flow cytometry. The parameters that will be studied are ultrasound intensity, flow rate, and concentration of the molecular probes. These measurements will be compared to identical measurements where the cells are exposed only to a single ultrasound beam. The effect of the contrast agents in loading will also be investigated by adding the contrast agents into the extracellular medium and measure the amount of molecular probes that are loaded into the cells.

The influx of molecules present in the extracellular medium can also be measured to determine the loading efficiency of the beat frequency. RBC will be flown inside the tube and exposed to the difference frequency. Probe molecules (fluorescence-labeled dextran $4_1$, 12 or 70 kDa molecular weight) will be added to the extracellular medium. The uptake of the molecular probes will be determined by flow cytometry. The parameters that will be studied are ultrasound intensity, time of exposure, concentration, and size of the molecular probes. These measurements will be compared to identical measurements in which the cells will be exposed only to a single ultrasound beam. The effect of contrast agents in enhancing molecular loading will also be investigated by adding contrast agents into the extracellular medium and measuring the number of molecules that are loaded into the cells. The effect of the cavitation on cell viability will be investigated with a tritiated thymidine assay. The incorporation of thymidine will be measured as a function of intensity, flow rate, and concentration of the contrast agent.

REFERENCES CITED

1. Anderson R R, Optics of the skin, in Clinical Photomedicine, Lim H W, Sotel N A, Ed., Marcel Dekker, NY (1993).
2. Jarry G, Poupinet L, Watson J, Lepine T, Extinction measurements in diffusing tissue with heterodyne detection and a titanium: sapphire laser, Applied Optics 34:2045–2054.
3. Moan J, Peng Q, Sorensen R, Iani V, Nesland J M, The biophysical foundations of photodynamic therapy, Endoscopy 30:387–391 (1998).
4. Yoon G, Welch A J, Motamedi M, Van Gemert M C J, Development and application of three-dimensional light distribution model for laser irradiated tissue, IEEE J Quant Electron QE-23: 1721–1733 (1987).
5. Payne B P, Nishioka N S, Mikic B B, Venugopalan V, Comparison of pulsed $CO_2$ laser ablation at 10.6 μm and 9.5 μm, Lasers Surg Med 23:1–6 (1998).
6. Yamanouchi K, Tsuchiya S, Tunable vacuum ultraviolet laser spectroscopy: excited state dynamics of jet-cooled molecules and van der waals complexs, J Phys B 28:133–165 (1995).
7. Bjorklund G C, Effects of focusing on third-order nonlinear processes in isotropic media, IEEE J Quant Electron QE-I 1:287–296 (1975).
8. Levine B F, Bethea C G, Effects on hyperpolarizabilities of molecular interactions in associating liquid mixtures, J Chem Phys 65:2429–2438 (1976).
9. CRC Handbook of Chemistry and Physics, 79th Edition. Lide D R, Ed. CRC Press, New York.
10. Jacques S L, Prahl S A, Modeling optical and thennal distributions in tissue during laser irradiation. Lasers Surg Med 6:494–503 (1987).
11. S B Barnett, H-D Rott, G R ter Haar, M C Ziskin, K Maeda. The sensitivity of biological tissue to ultrasound. Ultrasound Med Biol., 23:805–812 (1997).
12. K S Suslick, ed: "Ultrasound: Its chemical, physical and biological effects." VCH, New York, 1988.
13. M W Miller, D L Miller, A B Brayman. "A review of in vitro bioeffects of inertial ultrasonic cavitation from a mechanistic perspective." Ultrasound Med Biol., 22:1131–1154 (1996).
14. T R Morgan, V P Laudone, W D W Heston, L Zeitz, W F Fair. "Free radical production by high energy shock waves-comparison with ionizing radiation." J Urol., 139:186–189 (1988).
15. R E Apfel, C K Holland. "Gauging the likelihood of cavitation from short-pulse, low duty cycle diagnostic ultrasound." Ultrasound Med Biol., 17:170–185 (1991).
16. J Ophir, K J Parker. "Contrast agents in diagnostic ultrasound. " Ultrasound Med Biol., 15:319–333 (1989).
17. D L Miller, R T Thomas. "Ultrasound contrast agents nucleate inertial cavitation in vitro." Ultrasound Med Biol., 21:1059–1065 (1995).
18. J Liu, T N Lewis, M R Prausnitz. "Non-invasive assessment and control of ultrasound-mediated membrane permeabilization." Pharm. Res., 15:918–924 (1998).
19. H J Kim, J F Greenleaf, R R Kinnick, J T Bronk, M E Bolander. "Ultrasound-mediated transfection of mammalian cells." Human Gene Therapy, 7:1339–1346 (1996).
20. K I Morton, G R ter Haar, I J Stratford, C R Hill. "The role of cavitation in the interaction of ultrasound with V79 Chinese hamster cells in vitro." Br. J Cancer, (45 suppl V): 147–150, (1982).
21. M Delius, F Ueberle, S Gambihler. "Acoustic energy determines hemoglobin release from erythrocytes by extracorporeal shock waves in vitro." Ultrasound Med Biol., 21:707–710 (1995).
22. S Lee, D J McAuliffe, H Zhang, Z Xu, J Taitelbaum. T J Flotte, A G Doukas. "Stress-wave-induced membrane permeation of red blood cells is facilitated by aquaporins." Ultrasound Med Biol., 23:1089–1094 (1997).

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. An apparatus for treating tissue using two different wavelengths, comprising a first energy emitter which produces a first wavelength of energy and a second energy emitter which produces a second wavelength of a second energy, such that said first and second wavelengths are focused onto a focal point or region of a tissue, such that said first and second wavelengths produce an overlap region in which the first and second wavelengths mix to form a third wavelength which produces cavitation and/or hyperthermia at said focal point or region within said tissue.

2. The apparatus of claim 1, wherein said first and second energy emitters are lasers.

3. The apparatus of claim 2, wherein said lasers are ND:YAG lasers.

4. The apparatus of claim 2, wherein said piezoelectric transducers are ceramic.

5. The apparatus of claim 1, wherein said first wavelength is about 1.06 $\mu$m and said second wavelength is between about 550 nm and 920 nm.

6. The apparatus of claim 1, wherein said energy difference is between about 3 and 6.5 $\mu$m.

7. The apparatus of claim 1, wherein said first and second energy emitters are piezoelectric transducers.

8. The apparatus of claim 1, wherein said first wavelength of energy has a frequency of about 3.8 MHZ and said second wavelength of energy has a frequency of about 4.0 MHZ.

9. The apparatus of claim 1, wherein said two different wavelengths of energy are ultrasonic signals having a frequency difference of about 200 kHz.

10. The apparatus of claim 9, wherein said wavelengths mix to form a signal with a subharmonic frequency of about 100 kHz.

11. An apparatus for treating tissue using two different wavelengths, comprising
   a) a first energy emitter which produces a first wavelength of energy;
   b) a second energy emitter which produces a second wavelength of a second energy; and
   c) a control means for said apparatus to carry out treatment, wherein said control means causes transmission and focusing of said first and second wavelengths onto a focal point or region of a tissue, whereby said first and second wavelengths produce an overlap region having an energy difference which produces energy of a third wavelength effective to provide cavitation an/or hyperthermia at said focal point or region within said tissue.

12. The apparatus of claim 11, wherein said control means causes transmission of ultrasonic waves for a duration of between about 1 millisecond and continuous.

13. The apparatus of claim 11, wherein said control means provides transmission of ultrasonic waves by successive pulses.

14. A method for treating tissue using two different wavelengths, comprising the steps of:
   a) directing a first wavelength of energy into a tissue; and
   b) directing a second wavelength of a second energy into said tissue, such that said first and second wavelengths are focused onto a focal point or region of said tissue in an overlap region having an energy difference which produces a third wavelength that effectively couples energy to said tissue to provide cavitation and/or hyperthermia at said focal point or region within said tissue, thereby treating said tissue.

15. The method of claim 14, wherein the steps of directing said first and second wavelengths of energy are performed by directing lasers.

16. The method of claim 15, wherein said lasers are ND:YAG lasers.

17. The method of claim 14, wherein said first wavelength is about 1.06 $\mu$m and said second wavelength is between about 558 nm and 920 nm.

18. The method of claim 14, wherein said energy difference is between about 3 and 6.5 $\mu$m.

19. The method of claim 14, wherein said first and second energy emitters are piezoelectric transducers.

20. The method of claim 19, wherein said piezoelectric transducers are ceramic.

21. The method of claim 14, wherein said first wavelength is about 3.8 MHZ and said second wavelength is about 4.0 MHZ.

22. The method of claim 14, wherein said energy difference is about 200 kHz.

23. The method of claim 22, wherein said energy difference has a subharmonic frequency of about 100 kHz.

24. The method of claim 14, wherein said energy wavelengths are pulsed for a duration of between about 1 millisecond and continuous.

25. A method of treating tissue, such method comprising the step of directing first and second wavelengths of energy into an overlap region of tissue such that the first and second wavelengths mix in situ to form a third wavelength, wherein the third wavelength effectively couples energy into the tissue to treat tissue in said overlap region.

* * * * *

UNITED STATES PATENT AND TRADEMARK OFFICE
CERTIFICATE OF CORRECTION

PATENT NO. : 6,428,532 B1
APPLICATION NO. : 09/460860
DATED : August 6, 2002
INVENTOR(S) : Shun Lee and Apostolos Doukas It is certified that error appears in the above-identified patent and that said Letters Patent is hereby corrected as shown below:

\*\* In the Specification:

At column 1, line 5, before "BACKGROUND OF THE INVENTION", insert the following:

--STATEMENT REGARDING FEDERALLY SPONSORED RESEARCH

This invention was made with Government support under Grant No. N00014-94-1-0927 awarded by the U.S. Department of the Navy. The U.S. Government has certain rights in this invention.--

Signed and Sealed this

Seventh Day of July, 2009

JOHN DOLL
*Acting Director of the United States Patent and Trademark Office*